United States Patent [19]
Matsushima et al.

[11] Patent Number: 5,981,486
[45] Date of Patent: Nov. 9, 1999

[54] PEPTIDE SUPPRESSING IκBα PHOSPHORYLATION

[75] Inventors: Kouji Matsushima, Kanazawa; Yuji Ishikawa, Gotenba; Kouji Kuno, Kanazawa, all of Japan

[73] Assignee: Chugai Seiyaku Kabushiki Kaisha, Tokyo, Japan

[21] Appl. No.: 08/930,605

[22] PCT Filed: Apr. 12, 1996

[86] PCT No.: PCT/JP96/01028

§ 371 Date: Oct. 14, 1997

§ 102(e) Date: Oct. 14, 1997

[87] PCT Pub. No.: WO96/32412

PCT Pub. Date: Oct. 17, 1996

[30] Foreign Application Priority Data

Apr. 13, 1995 [JP] Japan ................................ 7-111033

[51] Int. Cl.⁶ .......................... A61K 38/00; A61K 38/04
[52] U.S. Cl. ................... 514/12; 514/13; 514/14; 514/17; 530/324; 530/326; 530/327; 530/329
[58] Field of Search ....................... 435/320.1; 536/23.5; 530/324, 326, 327, 329, 350; 514/12, 13, 14, 17

[56] References Cited

FOREIGN PATENT DOCUMENTS

| | | |
|---|---|---|
| 0 779 361 | 6/1997 | European Pat. Off. . |
| 9-216898 | 8/1997 | Japan . |
| 97/30712 | 8/1997 | WIPO . |

OTHER PUBLICATIONS

Barroga et al., "Constitutive phosphorylation of IkBα by casein kinase II". *Proc. Natl. Acad Sci. USA* 92: 7637–7641 (1995).

Kuno et al., Identification of an Ikbα–associated Protein Kinase in a Human Monocytic Cell Line and Determination of its Phosphorylation Sites on IkB–$_\alpha$. *The Journal of Biological Chemistry* 270: 27914–27919 (1995).

"Proceedings of the Japanese Society for Immunology" vol. 25 p. 156 (1995) English Translation.

*Primary Examiner*—Robert A. Wax
*Assistant Examiner*—Elizabeth Slobodyansky
*Attorney, Agent, or Firm*—Foley & Lardner

[57] ABSTRACT

The present invention discloses an antiinflamatory agent or immunosuppressant that contains as its active ingredient a peptide that inhibits phosphorylation of IκBα, an example of which is the peptide having the following amino acid sequence (SEQ ID NO: 1): Met-Leu-Pro-Glu-Ser-Glu-Asp-Glu-Glu-Ser-Tyr-Asp-Thr-Glu-Ser-Glu-Phe-Thr-Glu-Phe-Thr-Glu-Asp-Glu-Leu.

24 Claims, 7 Drawing Sheets

```
279                              303
MLPESEDEESYDTESEFTEFTFDEL
                              PYDD
 del-10                         307
       del-9

MLPEAEDEEAYDAEAEFAFFAEDEL   MUTANT K
```

PEPTIDE SUPPRESSING IκBα PHOSPHORYLATION

TECHNICAL FIELD

The present invention relates to a peptide capable of inhibiting phosphorylation of IκBα, and more particularly, to a peptide useful as an antiphlogistic or immunosuppressant.

BACKGROUND ART

A region referred to as κB and usually composed of 10 nucleotides was clearly shown to promote gene transcription activity as a part of an enhancer by analysis of the protein-binding region in the enhancer region of human immunodeficiency virus (HIV) and antibody κ light chain. When the transcription regulating protein, nuclear factor κB (NFκB) binds to this region, transcription of gene downstream from the κB region is promoted (Gilmore, T. & Morin, P. J.: Trends in Genetics (1993) 9, 427–432).

According to a study using a pre-B cell line, 70Z/3 cells, and Hela cells, it is known that these cells contain in their cytoplasm NFκB that does not have any DNA binding activity, and that by phorbol ester stimulation, the DNA binding activity is derepressed causing NFκB to translocate into the nucleus (Baeuerle, P. A. & Baltimore, D.: Cell (1988) 53, 211–217).

NFκB is a heterodimeric or homodimeric transcription factor comprising two subunits (p50, p65), and is induced by various stimuli. It is currently estimated to be involved in the transcription activity of more than 20 genes (Baeuerle, P. A.: Biochim. Biophys. Acta (1991) 1072; 63–80).

NFκB is also located upstream from the cytokine genes of Interleukin-8, Interleukin-1β, tumor necrosis factor (TNF)-α, Interleukin-6 and Interleukin-2 as well as cyclooxygenase-2 (Kujubu, D. A. et al., J. Biol. Chem. (1991) 266, 12866–12872) or 5-lipoxygenase (Hoshiko, S. et al., Proc. Natl. Acad. Sci. U.S.A. (1990) 87, 9073–9077; Chopra, A. et al., Biochem. Biophys. Res. Commun. (1992) 185, 489–495), which are enzymes involved in the biosynthesis of metabolites of the arachidonic acid cascade, mediators of inflammations, and the genes of adhesion factors such as ELAM-1 (endothelial leukocyte adhesion molecule-1) (Hooft van Huijsduijnen, R. et al., J. Biol. Chem. (1992) 267, 22385–22391) and VCAM-1 (Vascular Cell Adhesion Molecule-1) (Iademarco, M. F. et al., J. Biol. Chem. (1992) 267, 16323–16329). NFκB is considered to be involved in the control of the transcription of these genes.

The action of steroids, which are currently used as anti-inflammatory agents (Mukaida, N. et al., J. Biol. Chem. (1994) 269, 13289–13295) and the powerful immunosuppressant, FK-506 (Okamoto, S.-i. et al., J. Biol. Chem. (1994) 269, 8582–8589) is suggested to at least involve an inhibition of the activation of NFκB. In the cytoplasm, NFκB binds with protein IκBα, which inhibits the function of NFκB, resulting in inhibition of its activation (Inoue, J–I. et al., Proc. Natl. Acad. Sci. USA (1992) 89, 4333–4337; Hatada, E. et al., EMBO (1993) 12, 2781–2788).

Zabel, U. et al. reported to have isolated IκBα as a 37 kDa homogeneous protein from human placenta (Cell (1990) 61, 255–265). This was followed by the isolation of the cDNA of human IκBα (Sporn, S. A. et al., J. Immunol. (1990) 144, 4434–4441; Haskill, S. et al., Cell (1991) 65, 1281–1289, see WO 92-20795).

IκBα not only inhibits the binding of NFκB to DNA, but also inhibits the translocation of NFκB into the nucleus (Baeuerle, P. A. & Baltimore, B. Science (1988) 242, 540–546). IκBα has been clearly shown to be phosphorylated in response to various stimuli such as TNFα and so forth.

NFκB translocates into the nucleus and binds to the protein-binding site on DNA as a result of phosphorylation or degradation of IκBα in this manner or by phosphorylation of the proteins comprising NFκB, followed by activation of the transcription of genes located downstream (Baeuerle, P. A.: Biochim. Biophys. Acta (1991) 1072, 63–80). Although the above-mentioned mechanism is known to occur at the time of activation of NFκB, the enzyme group that phosphorylates NFκB and IκBα in vivo, the phosphorylation site and its detailed mechanism have not been determined.

DISCLOSURE OF THE INVENTION

So far steroids and other drugs have been used as antiinflammatory agent. Steroids have the risk of inducing adverse side effects including susceptibility to infection, diabetes and cataracts. Although nucleic acid synthesis inhibitors and similar drugs have been used as immunorepressors, these result in adverse side effects such as inhibition of bone marrow function, liver injury, susceptibility to infection and digestive tract disorders. Thus, there has been a desire to develop a drug that does not produce these types of adverse side effects.

The object of the present invention is to provide a peptide that inhibits phosphorylation of IκBα, comprised of the phosphorylation site of IκBα, for specifically inhibiting the gene expression of inflammatory cytokines and inflammatory mediators as well as the release of their gene products.

During the course of studying the mechanism of the activation of NFκB, the inventors of the present invention succeeded in identifying the phosphorylation site of IκBα by using various types of partially deleted mutants and substituted mutants of IκBα. Moreover, by placing a peptide corresponding with said phosphorylation site in the presence of IκBα, it was found that the phosphorylation of IκBα was inhibited, thereby inhibiting the activation of NFκB.

Thus, the present invention provides a peptide having an amino acid sequence corresponding to the phosphorylation site of IκBα, and its pharmacologically acceptable salts.

DETAILED DESCRIPTION

As is clear from Example 1 (2), the phosphorylation site of IκBα is surmised to be Ser (288), Thr (291) and Ser (293) in the sequence Ser (288)-Tyr (289)-Asp (290)-Thr (291)-Glu (292)-Ser (293)-Glu (294) (residues 10–16 of SEQ ID NO: 1) within the amino acid sequence of said protein. Thus, the peptide in the present invention that has the amino acid sequence corresponding with the phosphorylation site of IκBα and is able to inhibit the phosphorylation of IκBα is that consists of the amino acid sequence Ser-Tyr-Asp-Thr-Glu-Ser (residues 10–15 of SEQ ID NO: 1) (referred to as the core amino acid sequence), or comprises this core amino acid sequence.

Comprising this amino acid sequence refers to that in which the N-terminal side or C-terminal side, or both sides of the amino acid sequence are extended with amino acid or a peptide. The amino acid or peptide that extends the N-terminal and/or C-terminal may be any amino acid or peptide provided it inhibits phosphorylation of IκBα.

However, according to a preferable embodiment of the present invention, the amino acid or peptide that extends the N-terminal side and/or C-terminal side of the above-mentioned core amino acid sequence is that which is present in the amino acid sequence of IκBα and is adjacent to the above-mentioned core amino acid sequence. This means that the whole peptide composed of the core amino acid sequence and the terminal amino acid or amino acid sequence that extends it forms a portion of the amino acid sequence of IκBα.

If the amino acid sequence within IκBα is Met(279)-Leu (280)-Pro(281)-Glu(282)-Ser(283)-Glu(284)-Asp(285)-Glu (286)-Glu(287)-Ser(288)-Tyr(289)-Asp(290)-Thr(291)-Glu (292)-Ser(293)-Glu(294)-Phe(295)-Thr(296)-Glu(297)-Phe (298)-Thr(299)-Glu(300)-Asp(301)-Glu(302)-Leu(303) (SEQ ID NO: 1), an example of a peptide having this amino acid sequence comprises a portion of this sequence and has the following N-terminals and C-terminals:

Ser(288)-Glu(294), Ser(288)-Phe(295), Ser(288) -Thr (296), Ser(288)-Glu(297), Ser(288)-Phe(298), Ser (288)-Thr(299), Ser(288)-Glu(300), Ser(288)-Asp (301), Ser(288)-Glu(302), Ser(288)-Leu(303),

Glu(287)-Glu(294), Glu(287)-Phe(295), Glu(287)-Thr (296), Glu(287)-Glu(297), Glu(287)-Phe(298), Glu (287)-Thr(299), Glu 287)-Glu(300), Glu(287)-Asp (301), Glu(287)-Glu(302), Glu(287)-Leu(303),

Glu(286)-Glu(294), Glu(286)-Phe(295), Glu(286)-Thr (296), Glu(286)-Glu(297), Glu(286)-Phe(298), Glu (286)-Thr(299), Glu(286)-Glu(300), Glu(286)-Asp (301), Glu(286)-Glu(302), Glu(286)-Leu(303), Asp (285)-Glu(294), Asp(285)-Phe(295), Asp(285)-Thr (296), Asp(285)-Glu(297), Asp(285)-Phe(298), Asp (285)-Thr(299), Asp(285)-Glu(300), Asp(285)-Asp (301), Asp(285)-Glu(302), Asp(285)-Leu(303),

Glu(284)-Glu(294), Glu(284)-Phe(295), Glu(284)-Thr (296), Glu(284)-Glu(297), Glu(284)-Phe(298), Glu (284)-Thr(299), Glu(284)-Glu(300), Glu(284)-Asp (301), Glu(284)-Glu(302), Glu(284)-Leu(303),

Ser(283)-Glu(294), Ser(283)-Phe(295), Ser(283)-Thr (296), Ser(283)-Glu(297), Ser(283)-Phe(298), Ser (283)-Thr(299), Ser(283)-Glu(300), Ser(283)-Asp (301), Ser(283)-Glu(302), Ser(283)-Leu(303),

Glu(282)-Glu(294), Glu(282)-Phe(295), Glu(282)-Thr (296), Glu(282)-Glu(297), Glu(282)-Phe(298), Glu (282)-Thr(299), Glu(282)-Glu(300), Glu(282)-Asp (301), Glu(282)-Glu(302), Glu(282)-Leu(303),

Pro(281)-Glu(294), Pro(281)-Phe(295), Pro(281)-Thr (296), Pro(281)-Glu(297), Pro(281)-Phe(298), Pro( 281)-Thr(299), Pro(281)-Glu(300), Pro(281)-Asp (301), Pro(281)-Glu(302), Pro(281)-Leu(303),

Leu(280)-Glu(294), Leu(280)-Phe(295), Leu(280)-Thr (296), Leu(280)-Glu(297), Leu(280)-Phe(298), Leu (280)-Thr(299), Leu(280)-Glu(300), Leu(280)-Asp (301), Leu(280)-Glu(302), Leu(280)-Leu(303),

Met(279)-Glu(294), Met(279)-Phe(295), Met(279)-Thr (296), Met(279)-Glu(297), Met(279)-Phe(298), Met (279)-Thr(299), Met(279)-Glu(300), Met(279)-Asp (301), Met(279)-Glu(302), Met(279)-Leu(303).

The following are examples of peptides having an amino acid sequence as described above.

Peptides containing the amino acid sequence: Met-Leu-Pro-Glu-Ser-Glu-Asp-Glu-Glu-Ser-Tyr-Asp-Thr-Glu-Ser-Glu-Phe-Thr-Glu-Phe-Thr-Glu-Asp-Glu-Leu (SEQ ID NO: 1);

Peptides containing the amino acid sequence: Met-Leu-Pro-Glu-Ser-Glu-Asp-Glu-Glu-Ser-Tyr-Asp-Thr-Glu-Ser-Glu-Phe (SEQ ID NO: 2);

Peptides containing the amino acid sequence: Ser-Glu-Asp-Glu-Glu-Ser-Tyr-Asp-Thr-Glu-Ser-Glu-Phe (SEQ ID NO: 3); and Peptides containing the amino acid sequence: Ser-Tyr-Asp-Thr-Glu-Ser (SEQ ID NO: 4).

As the size of the peptide of the present invention becomes shorter, its immunogenicity inside the human body decreases while also being more resistant to decomposition by proteases in the body, thus making it advantageous.

In the above-mentioned amino acid sequence, Met indicates methionine, Leu leucine, Pro praline, Glu glutamate, Ser serine, Asp aspartate, Tyr tyrosine, Thr threonine and Phe phenylalanine, and all of said amino acids are in the L form.

The above-mentioned amino acid sequence of the peptide of the present invention may contain replacement, deletion and/or insertion provided it is able to inhibit the phosphorylation of IκBα.

Those targets of substitution, deletion and/or insertion within the core sequence are the amino acids Tyr, Asp and Glu which are not targets of phosphorylation. The number of targets of the amino acid is 1 to 2. However, it is preferable that the core amino acid sequence not be changed by substitution, deletion and/or insertion. The number of amino acids that can be changed by substitution, deletion and/or insertion in portions other than the core sequence may be 1 or more amino acids, and preferably less than half, more preferably less than 30%, and even more preferably less than 20%, for example 10% or less, of the total number of amino acids other than the core portion of said peptide.

The peptide of the present invention may also be modified. Here, modification refers to modification of the structure of the amino acids themselves that compose the peptide, modification of the crosslinking or peptide bonding between adjacent or non-adjacent amino acid residues, modification of the basic peptide backbone, introduction of side chain functional groups, ring formation and introduction of a spacer, etc. (Giannis, A. & Kolter, T.: Angrew. Chem. Ed. Engl. (1993) 32, 1244–1267).

Salts of the above-mentioned peptide may be any salt provided it is a pharmacologically acceptable acid addition salt or base addition salt. Examples of acid (inorganic acids and organic acids) addition salts include inorganic acid addition salts such as hydrochlorides, hydrogen bromides, sulfates and nitrates, and organic acid addition salts such as acetates, benzoates, maleates, fumarates, succinates, tartrates, citrates, oxalates, metasulfonates, toluenesulfonates, aspartates and glutamates. Examples of base (inorganic bases and organic bases) addition salts include inorganic base addition salts such as sodium salts, potassium salts and calcium salts, and organic base addition salts such as pyridine salts, triethylamine salts and lysine salts.

The peptide of the present invention can be produced by using methods routinely used in peptide synthesis, examples of which include liquid phase methods or solid phase methods (Peptide and Protein Drug Delivery, Lee, V. H. L. ed., Marcel Dekker, Inc. U.S.A.; Pharmaceutical Biotechnology, Borchardt, R. T. et al. ed., Prenum Press, New York and London). A starting material having a reactive carboxyl group corresponding to one of the two fragments that are designed by dividing at an arbitrary location of the peptide bond and synthesized by the above-mentioned method, and a starting material having a reactive amino group corresponding to another fragment, are condensed using the carboxyimide method or activated ester method and so forth, and in the case the condensation product that is formed has a protective group, that protective group is then removed to produce the peptide of the present invention.

Those functional groups that are not to be involved in the reaction in this reaction process are protected by protective groups. Examples of protective groups of amino groups include benzyloxycarbonyl, t-butyloxycarbonyl, p-biphenylisopropyloxycarbonyl and 9-fluorenylmethyloxycarbonyl groups. Examples of protective groups of carboxyl groups include groups that are able to form alkyl esters or benzyl esters and so forth. In the case of solid phase methods, however, the carboxyl group of the C-terminal is bonded to a carrier such as chlormethyl resin, oxymethyl resin or P-alkoxybenzylalcohol resin. The condensation reaction can be carried out in the presence of a condensation agent such as carboxyimide or an N-protected amino acid activated ester or peptide activated ester can be used. Although the protective groups are removed following completion of the condensation reaction, in the case of a solid phase method, the bond between the C-terminal of the peptide and the resin is also severed.

In addition, the peptide of the present invention can also be produced by using genetic engineering techniques (see the above-mentioned references Peptide and Protein Drug Delivery, and Pharmaceutical Biotechnology). For example, after synthesizing in accordance with routine methods a oligonucleotide coding for a desired amino acid sequence among the nucleotide sequence of IκBα disclosed in WO 92–20795, and assembling by PCR, it is introduced into a suitable expression vector. Next, suitable host cells are transformed with the expression vector.

Peptide is produced in a culture liquid or host cells by culturing the resulting transformed cells under suitable conditions. A nucleotide sequence coding for FLAG peptide (see WO 88–04692) or human immunoglobulin constant region (see WO 94–28027, Ellison, J. et al., DNA (1981) 1, 11–18; Krawinkel, U. et al., EMBO J. (1982) 1, 403–407) may be added to the nucleotide sequence coding for the peptide of the present invention, and it may be expressed in order to facilitate isolation and purification of the peptide that is produced or increase its stability.

Any expression system can be used for producing the peptide of the present invention, examples of which include eucaryotic cells such as animal cells including an established mammalian cell lines, fungal cells, yeast cells as well as procaryotic cells such as bacterial cells including *Escherichia coli*. Preferably, the peptide of the present invention is expressed in mammalian cells, examples of which include COS cells and CHO cells. In the case of using these cells, a routinely used promoter can be used that is useful for expressing in mammalian cells. For example, human cytomegalovirus immediate early promoter can be used.

Other promoters of gene expression in the mammalian cells that can be used for the present invention include viral promoters such as of retrovirus, polio virus, adenovirus and simian virus 40 (SV40), and promoters derived mammalian cells such as human polypeptide elongation factor-1α (HEF-1α).

Replication origins that can be used include those derived SV40, polio virus, adenovirus and bovine papilloma virus. Moreover, the expression vector may contain as a marker phosphotransferase APH(3')II or I (neo) gene, thymidine kinase (TK) gene, *E. coli* xanthine guanine phosphoribosyl transferase (Ecogpt) gene or dihydrofolate reductase (DHFR) and so forth to increase the number of gene copies in the host cells.

The peptide of the present invention is purified in accordance with routine methods, examples of which include ion exchange chromatography, reverse phase liquid chromatography and affinity chromatography. The amino acid sequence of peptides obtained in this manner can be analyzed with a protein sequencer and identified by acid type analysis using an amino acid analyzer.

The peptide of the present invention comprises the IκBα phosphorylation site and, provided it maintains the effect of inhibiting phosphorylation of IκBα, may contain replacement, deletion or insertion of amino acids. Moreover, its structure can also be modified to improve peptide stability, activity, half-life or cell membrane permeability (see Giannis, A. & Kolter, T.: Angew. Chem. Int. Ed. Engl. (1993) 32, 1244–1267). It is preferable that one modification of the peptide be made to have cell membrane permeability.

For example, the peptide of the present invention can be given cell membrane permeability by adding a lipolytic substance such as a steroid compound or compound having a benzene ring to its terminal. Moreover, the peptide of the present invention can also be used by encapsulating in a liposome to make it permeable to the cell membrane (see the above-mentioned Peptide and Protein Drug Delivery, Pharmaceutical Biotechnology).

In addition, the peptide of the present invention can also be expressed in the body by synthesizing an oligonucleotide coding for the amino acid sequence of the peptide of the present invention in accordance with routine methods, introducing it into a suitable expression vector in which it is able to be expressed, and administering into the body in accordance with known techniques (see WO 94–27643, WO 92–20316, Japanese Unexamined Patent Publication No. 6-303987, U.S. Pat. No. 5,166,320, WO 92–19749 and WO 92–20316, etc.). Alternatively, the peptide of the present invention can also be used ex vivo in gene therapy. Namely, the peptide of the present invention can be produced in transformed cells within the body by removing lymphocytes or other blood cells from the body, transforming these cells with the above-mentioned expression vector, and returning the transformed cells to the body (see Japanese Unexamined Patent Publication No. 6-329559).

Since the peptide of the present invention has the effect of inhibiting phosphorylation of IκBα, it is considered to inhibit the expression of inflammatory cytokine and inflammatory mediator genes as well as the release of their gene products. It is therefore effective in the treatment and prevention of inflammatory diseases of humans and other mammals and can also be used as an immunosuppressant. Moreover, since the peptide of the present invention is directed to the inhibition of NFκB activation by being targeted at inhibition of the phosphorylation of IκBα present in cells, its effects are surmised to be specific.

By using the peptide of the present invention as an antiphlogistic, it is expected to be useful in the treatment of various inflammatory diseases such as multiple sclerosis, systemic lupus erythematosus, articular rheumatism, psoriasis, gout, nephritis, inflammatory colitis, myocardial infarction, asthma, Mediterranean fever, Crohn's disease, adult respiratory distress syndrome, pulmonary emphysema, cystic fibrosis, hypersensitive pneumonia, tuberculous hydrothorax, carcinomatous hydrothorax, sarcoidosis, idiopathic fibroid lung, diffuse panbronchiolitis, following esophageal cancer surgery and ischemic reperfusion syndrome. In addition, the peptide of the present invention is also effective in the suppression of rejection reactions during bone marrow transplantation, organ transplantation and so forth by using as an immunosuppressant.

Although the peptide of the present invention may be administered by oral administration or parenteral administration, parenteral administration is particularly preferable. Examples of parenteral administration include injection, intrarectal administration, percutaneous administration and transpulmonary administration. Although the dose of the peptide of the present invention varies according to the administration method, patient symptoms, age and so forth, it is normally administered over the course of 1 to 4 administrations per day at 0.001 to 1000 mg, and preferably 0.01 to 10 mg, per administration.

The peptide of the present invention is normally administered in the form of a preparation formulated by mixing with a carrier or vehicle for pharmaceutical preparations (Remington's Pharmaceutical Science, Latest Edition, Mark Publishing Company, Easton, U.S.A.). Examples of preparation carriers and vehicles are those which are routinely used in the preparation field of pharmaceuticals, and substances that do not react with the peptide of the present invention. For example, when producing an injection preparation, pH adjusting agent such as hydrochloric acid, sodium hydroxide, sodium lactate, lactic acid, sodium hydrogen phosphate and sodium dihydrogen phosphate, isotonic agents such as sodium chloride and glucose, and the active ingredient in the form of the peptide of the present invention are dissolved as necessary in physiological saline for injection, and either filled into ampules following sterilization filtration, or freeze-dried in a vacuum after adding mannitol, dextrin, cyclodextrin, gelatin and so forth to prepare an injection preparation that is reconstituted at the time of use.

Alternatively, an emulsion for injection can also be prepared by adding lecithin, polysorbitol 80, polyoxyethylene hardened palm oil and so forth and emulsifying in water. When producing an intrarectal preparation, the active ingredient in the form of the peptide of the present invention along with a suppository base such as cacao butter, tri-, di- or monoglycerides of fatty acids or polyethyleneglycol are moisturized and dissolved, and poured into a mold followed either by cooling or coating with a gelatin film dissolved in polyethylene glycol or soy bean oil and so forth.

When producing a percutaneous preparation, white Vaseline, bees wax, liquid paraffin or polyethylene glycol and so forth are added to the active ingredient in the form of the peptide of the present invention as necessary followed by moisturizing and mixing to form an ointment, or after mixing with an adhesive such as rosin or alkylester acrylate polymer and so forth, spreading over a non-woven fabric of polyethylene and so forth to form a tape.

When manufacturing a transpulmonary preparation, the active ingredient in the form of the peptide of the present invention is dissolved or dispersed in an ordinary spray and filled into a pressurized container to form an aerosol.

Moreover, the peptide of the present invention can be prepared in the form of a continuous preparation by using known liposome technology and so forth.

In addition, the above-mentioned preparations may also contain other ingredients that are effective in the treatment of the target disease.

The following provides a detailed explanation of the present invention by describing Examples. However, the present invention is not limited to these Examples.

EXAMPLES

Reference Example 1

Preparation of Glutathione S-transferase (GST)-IκBα Fused Protein (1) Construction of DNA Coding for GST-IκBα Fused Protein In order to isolate the cDNA of human IκBα, specific primers GMD5 (SEQ ID NO: 5) and GMD3 (SEQ ID NO: 6) were synthesized with an oligonucleotide synthesizer for each of the nucleotide sequences in the vicinity of the start codon and stop codon, respectively, of IκBα cDNA based on the report of Haskill, S. et al. (Cell (1991) 65, 1281–1289). Furthermore, the primers were designed so that a site cleaved with restriction enzyme EcoRI was inserted in the 5'-end of primer GMD5, and a site cleaved with restriction enzyme BamHI was inserted in the 5'-end of primer GMD3. Total RNA was obtained from lipopolysaccharide (LPS)-stimulated human peripheral blood mononuclear cells using RNA zolB (Biotex Laboratory, Houston, U.S.A.).

Figure 1:
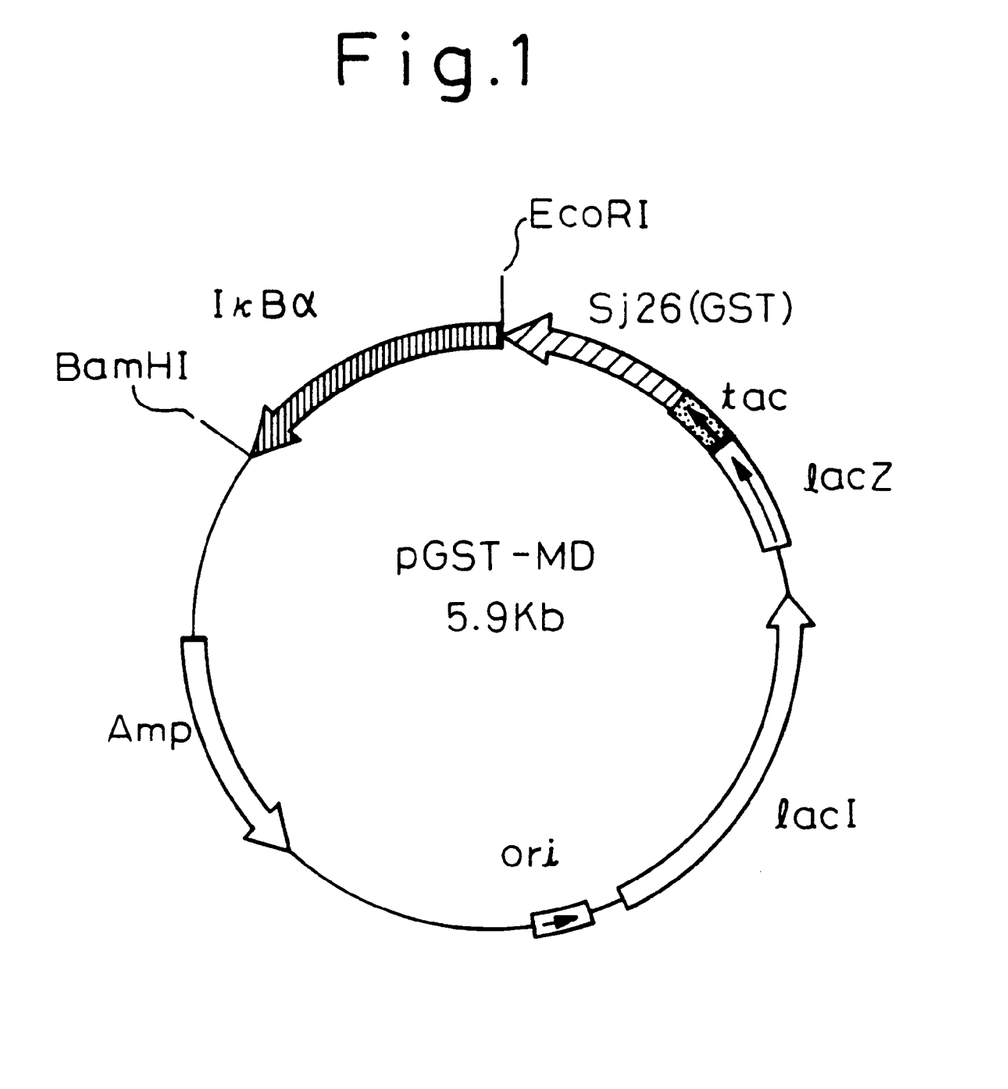
FIG. 1 schematically illustrates plasmid pGST-MD containing the glutathione-S transferase (GST) gene into which a DNA coding for the full length of human IκBα has been introduced.

Using the resulting total RNA as a template, reverse transcriptase-PCR (polymerase chain reaction) was performed using the above-mentioned primers GMD5 and GMD3 to obtain the entire length of human IκBα cDNA. The resulting entire length of human IκBα cDNA was introduced at the EcoRI and BamHI cleavage sites of plasmid vector pGENT2 containing glutathione S-transferase (GST) gene (Murakami, S. et al.: J. Biol. Chem. (1994) 269, 15118–15123) to obtain plasmid pGST-MD. The nucleotide sequence of the entire length of human IκBα cDNA was confirmed using the method of Sanger, F. et al. (Proc. Natl. Acad. Sci., USA (1977) 74, 5463–5467). A schematic drawing of plasmid pGST-MD is shown in FIG. 1.

(2) Construction of DNA Coding for GST-Partial Deletion IκBα Mutant Fused Proteins DNAs coding for six fused proteins comprising GST and six partial deletion mutants of IκBα were constructed using synthetic primers. Each primer had a nucleotide sequence corresponding to the respective deletion site. Primer GMD5 (SEQ ID NO: 5) and primer GMD6 (SEQ ID NO: 7) were designed so as to define each 5'-end and 3'-end of the DNA coding for mutant del-1 consisting of amino acids 1 to 242 of human IκBα. Primer GMD5 (SEQ ID NO: 5) and primer GMD7 (SEQ ID NO: 8) were designed so as to define each 5'-end and 3'-end of the DNA coding for mutant del-2 consisting of amino acids 1 to 181 of human IκBα.

Primer GMD52 (SEQ ID NO: 9) and primer GMD3 (SEQ ID NO: 6) were designed so as to define each 5'-end and 3'-end of the DNA coding for mutant del-4 consisting of amino acids 73 (1st ankirin repeat) to 317 of human IκBα. Primer GMD53 (SEQ ID NO: 10) and primer GMD3 (SEQ ID NO: 6) were designed so as to define each 5'-end and 3'-end of the DNA coding for mutant del-5 consisting of amino acids 182 (3rd ankirin repeat) to 317 of human IκBα.

Primer GMD5 (SEQ ID NO: 5) and primer GMD9 (SEQ ID NO: 11) were designed so as to define each 5'-end and 3'-end of the DNA coding for mutant del-9 consisting of amino acids 1 to 295 of human IκBα. Primer GMD5 (SEQ ID NO: 5) and primer GMD10 (SEQ ID NO: 12) were designed so as to define each 5'-end and 3'-end of the DNA coding for mutant del-10 consisting of amino acids 1 to 282 of human IκBα.

Figure 2:
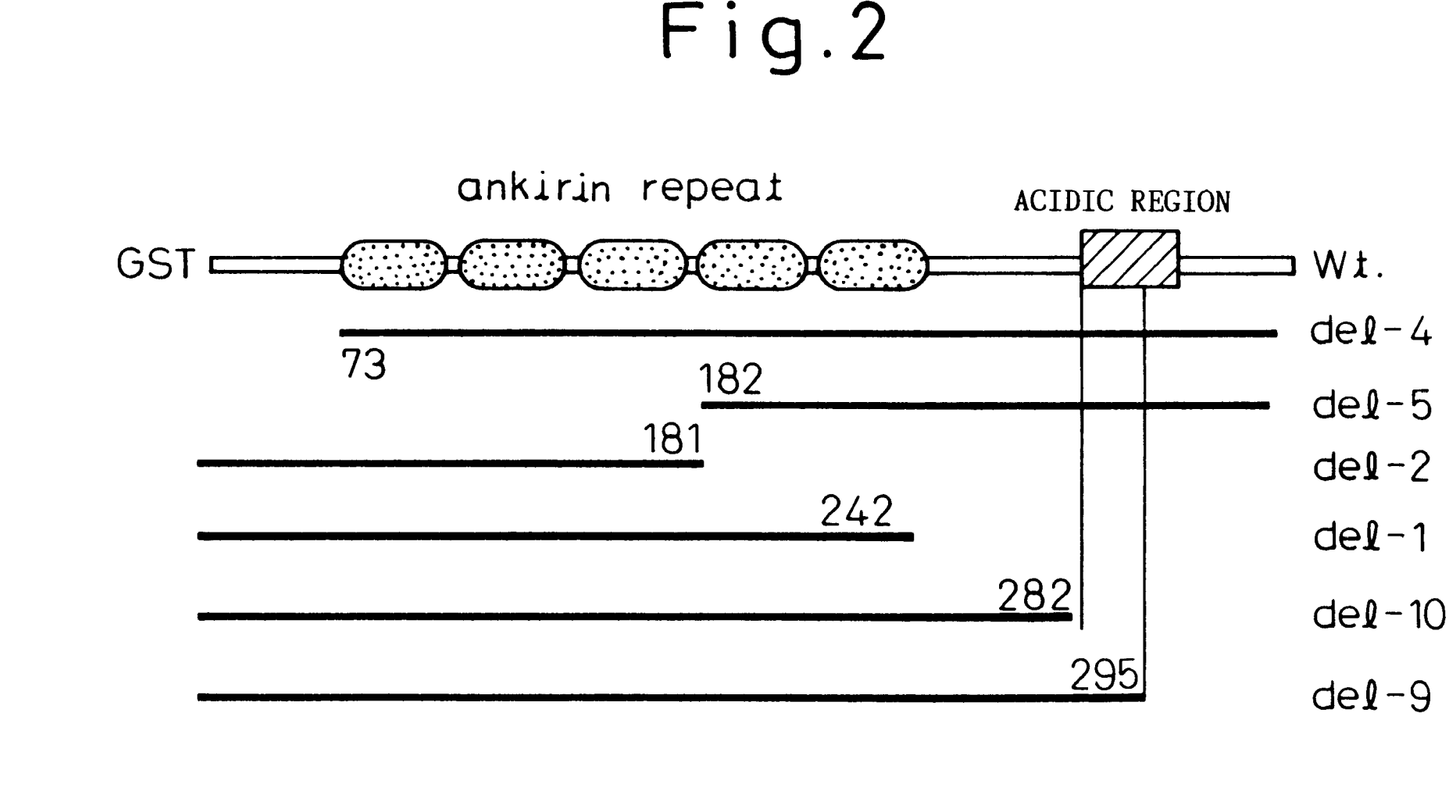
FIG. 2 schematically illustrates constructed fused proteins of various types of partially deleted IκBα mutants with GST.

Furthermore, each primer was designed so that a site cleaved by restriction enzyme EcoRI or BamHI was introduced on the 5'-end. Using plasmid vector pGENT2 containing the entire length of human IκBα cDNA as a template, PCR was performed using each primer pair that defines the 5'-end and 3'-end. The resulting DNA coding for each mutant was introduced into EcoRI and BamHI cleaved sites of plasmid vector pGENT2. The nucleotide sequence of each mutant cDNA was confirmed using the above-mentioned method of Sanger, F. et al. The structure of each mutant is schematically illustrated in FIG. 2.

(3) Construction of DNA Coding for GST-Substituted IκBα Mutant

DNA was constructed that codes for the fused protein consisting of GST and IκBα-mutant K (mt K) having a substitution mutation of the amino acids in the acidic region of the C-terminus of IκBα.

Figure 3:
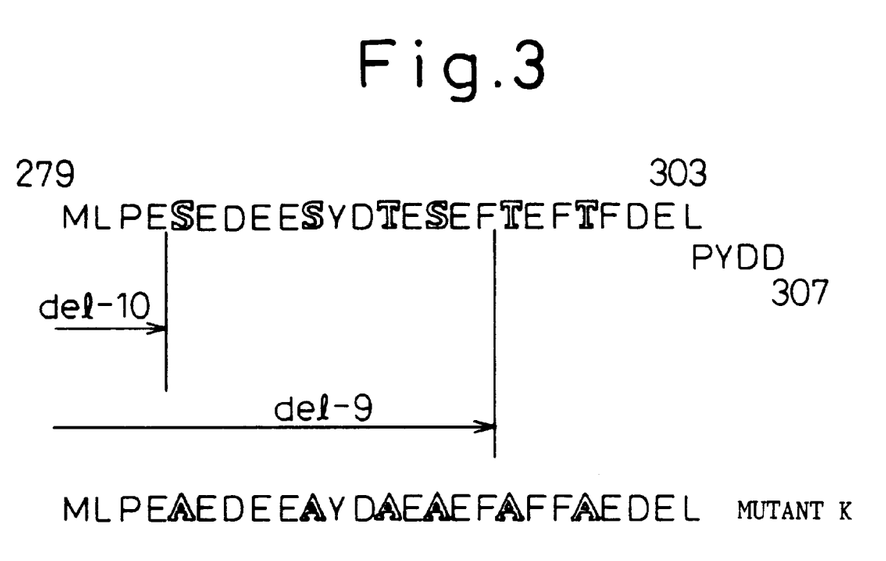
FIG. 3 schematically illustrates the amino acid sequences of the acidic regions present at the C-terminus of IκBα (SEQ ID NO: 19) and substituted IκBα mutant (SEQ ID NO: 20). Each symbol is an amino acid represented using single letter.

Using the animal cell expression vector, PRC/CMV, containing DNA coding for IκBα-mt K in which serine at position 283, serine at position 288, threonine at position 291, serine at position 293, threonine at position 296 and threonine at position 298 of the acidic region of the C-terminus are all substituted with analine (Ernst, M. K. et al.: Mol. Cell. Biol. (1995) 872–882) for the template, PCR was performed using specific primers GMD5 and GMD3 for the nucleotide sequences in the proximity of the start codon and stop codon of IκBα cDNA. The resulting DNA coding for IκBα substituted mutant-mt K was introduced into the sites cleaved with EcoRI and BamHI of plasmid vector pGENT2. The nucleotide sequence of the cDNA of mutant mt K was confirmed using the above-mentioned method of Sanger. F. et al. A schematic drawing of the acidic region of IκBα-mutant K is shown in FIG. 3.

(4) Preparation of GST-IκBα Fused Protein

Each of the expression vectors obtained in the above-mentioned steps (1), (2) and (3) were expressed in *Escherichia coli* to obtain GST-IκBα fused proteins.

After transforming *Escherichia coli* (JM109) with each expression vector, the microorganisms were cultured in 2×YT culture medium (Wako Pure Chemical Industries, Ltd.) containing 50 µg/ml of ampicillin. The microorganisms were stimulated by addition of 1 mM isopropylthiogalactoside (IPTG, Wako Pure Chemical Industries, Ltd.) after which the microorganisms were collected 2 to 3 hours later.

After separating by centrifugation, the pellet was washed with PBS(-) (Nissui Pharmaceutical Co., Ltd.). After pulverizing the pellet with ultrasonic waves in PBS(-) containing 1% Triton X-100 (Wako Pure Chemical Industries, Ltd.), the suspension was separated by centrifugation and the supernatant was recovered. Next, each fused protein was bound to glutathione sepharose (Pharmacia) equilibrated with PBS(-) containing 1% Triton X-100, and after washing five times with PBS(-), was eluted with 5 mM glutathione solution (Wako Pure Chemical Industries, Ltd.) (Smith, D. B. & Johnson, K. S.: Gene (1986) 67, 31–40).

Reference Example 2

Partial Purification of IκBα Phosphorylase (Kinase)

The kinase that phosphorylates IκBα was partially purified from human monocytic cell line THP-1. THP-1 cells were cultured at 37° C. and in the presence of 5% $CO_2$ in RPMI-1640 culture medium (Gibco BRL) containing 5% fetal calf serum (FCS, ICN Corp., Australia), 100 U/ml penicillin (Gibco BRL), 100 µg/ml streptomycin (Gibco BRL) and 2 mM L-glutamine (Wako Pure Chemical Industries, Ltd.). $4 \times 10^9$ THP-1 cells were stimulated for 5 minutes with 10 µg/ml LPS (*E. coli* 055-B5, Difco) and collected by centrifugation.

After washing the cell sediment twice with PBS(-), the sediment was suspended in 20 mM Hepes buffer (pH 7.9) containing 0.5 mM phenylmethylsulfonylfluoride (PMSF) and 1 µg/ml each of aprotinin, leupeptin and pepstatin (Sigma) followed by ultrasonic pulverization and centrifugation for 10 minutes at 500×g. The supernatant was further centrifuged for 35 minutes at 4° C. and 18000×g and dialyzed for 4 hours at 4° C. against 20 mM Tris buffer (pH 7.5) to obtain the crude fraction.

Next, the crude fraction was separated by elution by increasing the NaCl concentration in stepwise fashion at 0 M, 0.5 M and 2 M using a Red-A sepharose column (Amicon, bed volume: 5 ml) equilibrated with 20 mM Tris buffer (pH 7.5). The fraction eluted with 2 M NaCl was dialyzed for 4 hours at 4° C. against 20 mM Tris buffer (pH 7.5). This fraction was separated by elution by increasing the NaCl concentration in stepwise fashion at 0 M, 0.1 M, 0.25 M, 0.5 M and 2 M using a dimethylaminoethyl (DEAE) sephacel column (Pharmacia, bed volume: 20 ml) equilibrated with 20 mM Tris buffer (pH 7.5). After dialyzing the fraction eluting at 0.25 M NaCl for 4 hours at 4° C. against 20 mM Tris buffer (pH 7.5), the resulting fraction was eluted at the rate of 1 ml/min with DEAE-HPLC (DEAE-5PW, Tosoh) equilibrated with 20 mM Tris buffer (pH 7.5).

Fractions were collected in 2 ml aliquots while applying a linear concentration gradient from 0 to 0.5 M NaCl from 10 to 70 minutes after the start of elution. The activity of the resulting kinase was assayed using in vitro kinase assay (see Embodiment 1(1)) in the solid phase using glutathione sepharose coupled with GST-IκBα. The amount of protein was assayed using Coomassie Protein Reagent (Pierce) and bovine serum albumin (BSA) for the standard. As a result, the resulting partially purified IκBα kinase was purified by a factor of approximately 126 times (see Table 1).

| Step | Protein content (mg) | Activity ($\times 10^{-6}$ cpm) | Specific activity ($\times 10^{-6}$ cpm) | Purification (times) |
|---|---|---|---|---|
| Crude fraction | 126.16 | 104.4 | 0.83 | 1 |
| Red-A Sepharose (0.5–2M NaCl) | 9.73 | 66.7 | 6.86 | 8.26 |
| DEAE-sephacel (0.1–0.25M NaCl) | 4.54 | 64.3 | 14.16 | 17.6 |
| DEAE-HPLC (fr. 17–20) | 0.41 | 41.7 | 104.24 | 125.60 |

Example 1

Measurement of Phosphorylation Activity Against IκBα

(1) Experiment Using GST-IκBα Fused Protein

The phosphorylation activity against IκBα was measured by in vitro kinase assay. Each of the fused proteins prepared in Reference Example 1 and glutathione Sepharose beads (Pharmacia) were coupled by stirring for 2 hours at 4° C. and suspended in PBS(-) after washing three times with PBS(-) containing 1% NP-40 (Nakarai-Tesk) and twice with PBS (-). 20 μl of glutathione Sepharose beads containing 14 pmoles of fused protein, and 2 μl of purified IκBα kinase derived from the cytoplasm fraction obtained in the above-mentioned Reference Example 2 were prepared to 400 μl with PBS(-) followed by stirring for 3 hours at 4° C.

Next, precipitate was obtained by washing twice with PBS(-) containing 1% NP-40 and once with PBS(-). 5 μCi (185 kBq) of [γ-32P]ATP (Amersham Japan, #PB10168, 3000 Ci/mM) and 20 μl of kinase buffer (20 mM Hepes buffer containing 20 mM $MgCl_2$ and 10 mM $MnCl_2$ (pH 7.4)) were added to this precipitate and incubated for 5 minutes at 30° C. The reaction was stopped by adding PBS(-) containing 13.5 mM EDTA and 1% NP-40 followed by washing four times with PBS(-) containing 1% NP-40, adding 5 μl of sodium dodecyl sulfate (SDS) sample buffer (0.0625 M Tris-HCl (pH 6.8), 10% (w/v) glycerol, 5% (w/v) β-mercaptoethanol, 2.3% (w/v) SDS), and eluting protein in boiling water.

Figure 4:
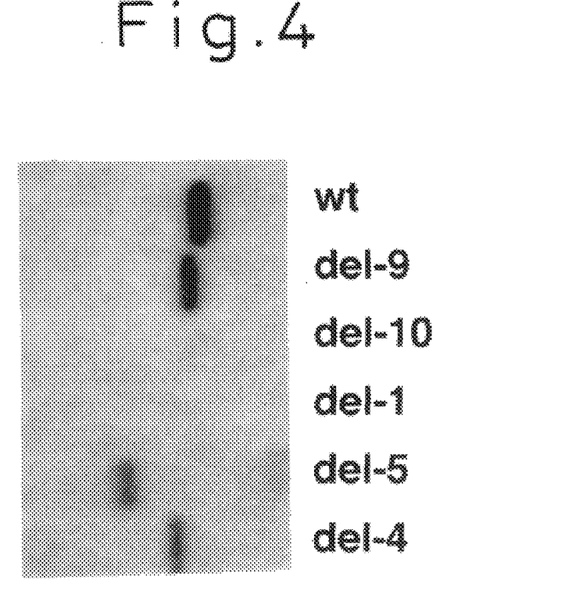
FIG. 4 is a diagram of electrophoresis of the phosphorylation of GST fused proteins of the full length of IκBα (wt) as well as deleted mutants del-9, del-10, del-1, del-5 and del-4 as determined by in vitro kinase assay in the solid phase.

After separating by centrifugation, the supernatant was applied on SDS-polyacrylamide electrophoresis (PAGE). Following completion of SDS-PAGE, autoradiography was performed using X-ray film (see FIG. 4). As a result, although radioactivity was detected in the cases of using fused proteins with GST of the entire length of IκBα (wild type; wt), mutant del-9, del-5 or del-4, radioactivity was not detected in the case of using fused proteins of GST and mutant del-10 or del-1.

Figure 5:
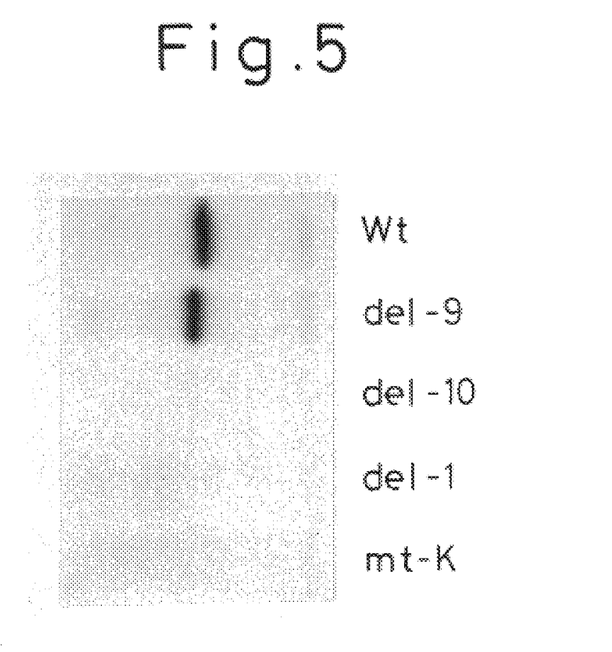
FIG. 5 is a diagram of electrophoresis of the phosphorylation of GST fused proteins of the full length of IκBα (wt) and deleted mutants del-9, del-10 and del-1 and a substituted mutant (mt-K) as determined by in vitro kinase assay in the liquid phase.

In addition, in a portion of the experiment, the above-mentioned kinase buffer was added to 14 pmoles of fused protein and 2 μl of partially purified IκBα kinase derived from the cytoplasm fraction of THP-1 cells without using glutathione Sepharose beads so that the final concentrations were equal after which assay was performed as described above with the liquid phase (see FIG. 5). As a result, although radioactivity was detected in the cases of using each fused protein of GST and the entire length of IκBα (wt) and del-9, radioactivity was not detected in the cases of using fused proteins of GST and mutant del-10, del-1 and substitution mutant (mt-K). These results clearly showed that the phosphorylation site exists in a region in which the amino acid sequences of mutants del-10 and of del-9 differ, and that IκBα is not phosphorylated when amino acid substitution is present in substitution mutant mt K.

(2) Competitive Inhibition of Phosphorylation Activity by Peptide

A peptide of the IκBα phosphorylation site having the amino acid sequence of SEQ ID NO: 1 was synthesized using a peptide synthesizer and purified by reverse phase HPLC after which its sequence was confirmed using an amino acid analyzer. The phosphorylation activity of IκBα was then assayed using this peptide.

Figure 6:
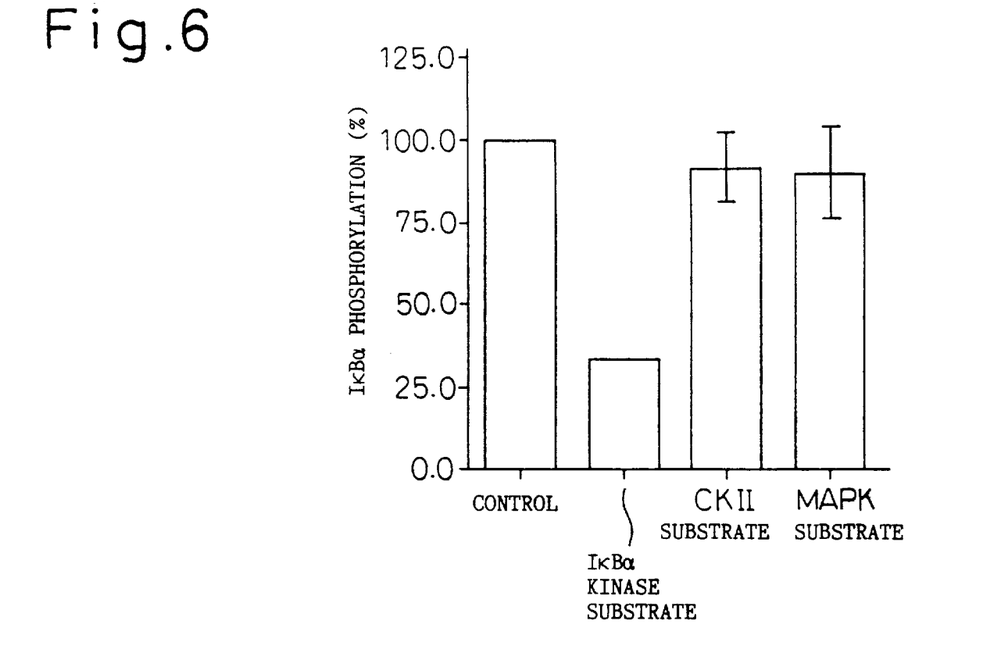
FIG. 6 illustrates the phosphorylation state of IκBα in an in vitro kinase assay in the case wherein the peptide corresponding with the phosphorylation site of IκBα (IκBα kinase substrate) and unrelated peptides which are casein kinase substrate (CKII substrate) and MAP kinase substrate (MAPK substrate) were added. The phosphorylation of each treatment when that of the control (peptide non-addition group) is taken to be 100% is expressed as a relative ratio (n=3).

An equal amount of the above-mentioned purified IκBα kinase derived from the cytoplasm fraction of THP-1 cells was added to fused protein of GST and IκBα (wt) followed by the addition of 2.7 nM of peptide (200 times the molar ratio) and assaying in the same manner as in (1) above. Those results are shown in FIG. 6. Phosphorylation of IκBα was inhibited by the addition of peptide of the IκBα phosphorylation site.

(3) Identification of Phosphorylation Site

In order to further identify the phosphorylation site of IκBα phosphorylation inhibitory peptide, in vitro kinase assay was performed using peptides in which one amino acid residue was substituted in the IκBα phosphorylation inhibitory peptide (SEQ ID NO: 1) prepared in Example 1(2).

An assay was performed in a liquid phase using the same conditions as in the in vitro kinase assay of Example 1(2) using 15 nmoles each of peptides in which serine at position 283, serine at position 288, threonine at position 291 or serine at position 293, which are expected to be the amino acid residues that are phosphorylated in the amino acid sequence of IκBα phosphorylation inhibitory peptide having the amino acid sequence of SEQ ID NO: 1, was substituted with one alanine residue each (283 Ala (SEQ ID NO: 13), 288 Ala (SEQ ID NO: 14), 291 Ala (SEQ ID NO: 15) or 293 Ala (SEQ ID NO: 16), respectively) (n=4). Furthermore, a positive control in which the entire length of IκBα (wt) was added and a negative control in which IκBα was not added were used as controls.

Figure 7:
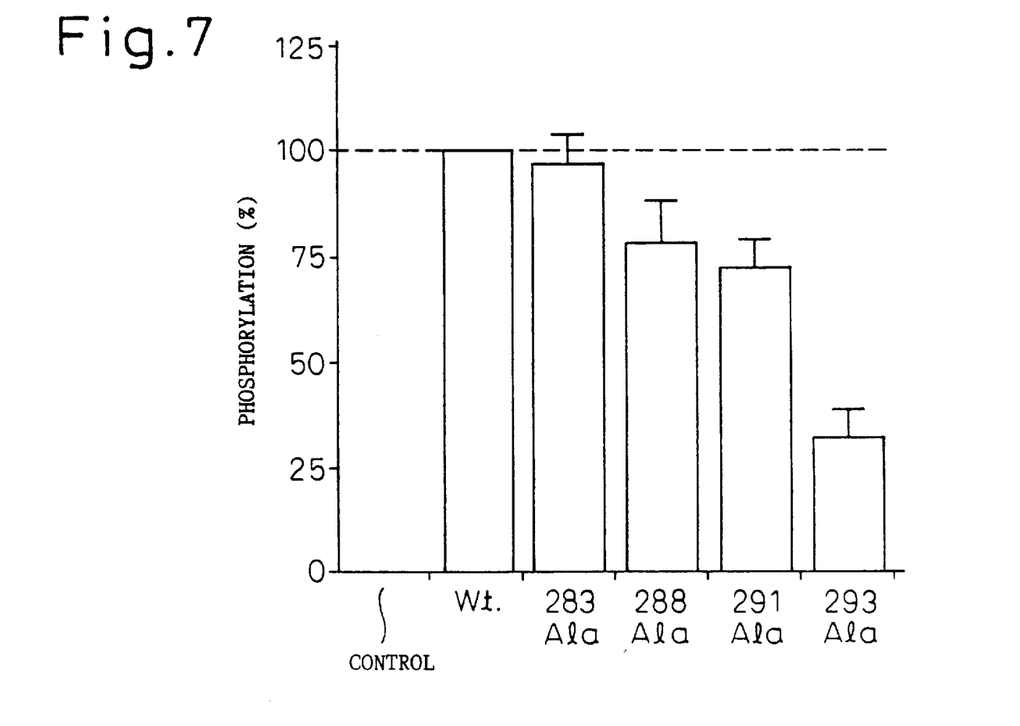
FIG. 7 illustrates the degree of phosphorylation of each amino acid-substituted peptide caused by the partially purified IκBα phosphorylase (kinase). The degree of phosphorylation of each peptide addition group when that of the positive control (group to which was added the peptide correspondig with the phosphorylation site of IκBα) is taken to be 100% is expressed as a relative ratio.

Following the assay, SDS polyacrylamide gel electrophoresis was performed in the same manner as Example 1(1) using Tris/Tricine buffer. The results were analyzed and quantified with an image analyzer (BAS1000, Fuji Film Co., Ltd.). Those results are shown in FIG. 7. As a result, peptide 283 Ala did not have an effect on phosphorylation. On the other hand, peptide 293 Ala had a significant effect on phosphorylation. In addition, peptides 288 Ala and 291 Ala only had a slight effect on phosphorylation.

Based on the above results, it was strongly suggested that serine at position 288, threonine at position 291 and serine at position 293 of the four serine or threonine residues in the amino acid sequence of IκBα phosphorylation inhibitory peptide are participated in the phosphorylation.

Furthermore, the reason why phosphorylation was not completely inhibited when each of the above-mentioned IκBα substituted mutants was used is thought to be because a serine or threonine residue other than the substituted amino acid residue was phosphorylated.

Example 2

Effect of Peptide of the IκBα Phosphorylation Site on NFκB Activity

The effect on NFκB activation in a cell-free system (Ishikawa, Y. et al., J. Biol. Chem. (1995) 362, 79–83) was investigated using peptides of the IκBα phosphorylation site.

Non-stimulated THP-1 cells were cultured under the conditions described in Reference Example 2. The cytoplasmic fraction and plasma membrane enriched fraction were prepared from THP-1 cells in accordance with the method of Sadowski, H. B. et al. (Nature (1993) 362, 79–83). Both 20 μg fractions were combined followed by the addition of 15 nM IκBα phosphorylation site peptide, 10 mM ATP and 20 μg/ml of LPS and stimulation for 10 minutes at 30° C.

After stopping the reaction by adding 13.5 mM EDTA (pH 8.0), the supernatant was obtained by centrifugal separation. Gel shift assay was performed on this supernatant using a $^{32}$P-labeled DNA probe containing the IL-8κB binding site in 0.25×TBE (final concentrations: 13.5 g Tris salt (Sigma), 6.9 g boric acid (Wako Pure Chemical Industries, Ltd.) and 1.165 g EDTA (Wako Pure Chemical Industries, Ltd.) per liter) containing 6% polyacrylamide gel (Acrylamide: bis=30:1) (Mukaida, N. et al., J. Biol. Chem. (1994) 269, 13289–13295). This was followed by analysis and quantification with an image analyzer (BAS1000, Fuji Film Co., Ltd.).

Furthermore, a control group to which LPS was not added, and groups to which were added 15 nM each of casein kinase 11 substrate (Kaengel, E. A. et al., J. Biol. Chem. (1987) 262, 9136–9140) (SEQ ID NO: 17) and MAP kinase substrate (Dong, Z. et al., J. Exp. Med. (1993) 177, 1071–1077) (SEQ ID NO: 18) were used.

Figure 8:
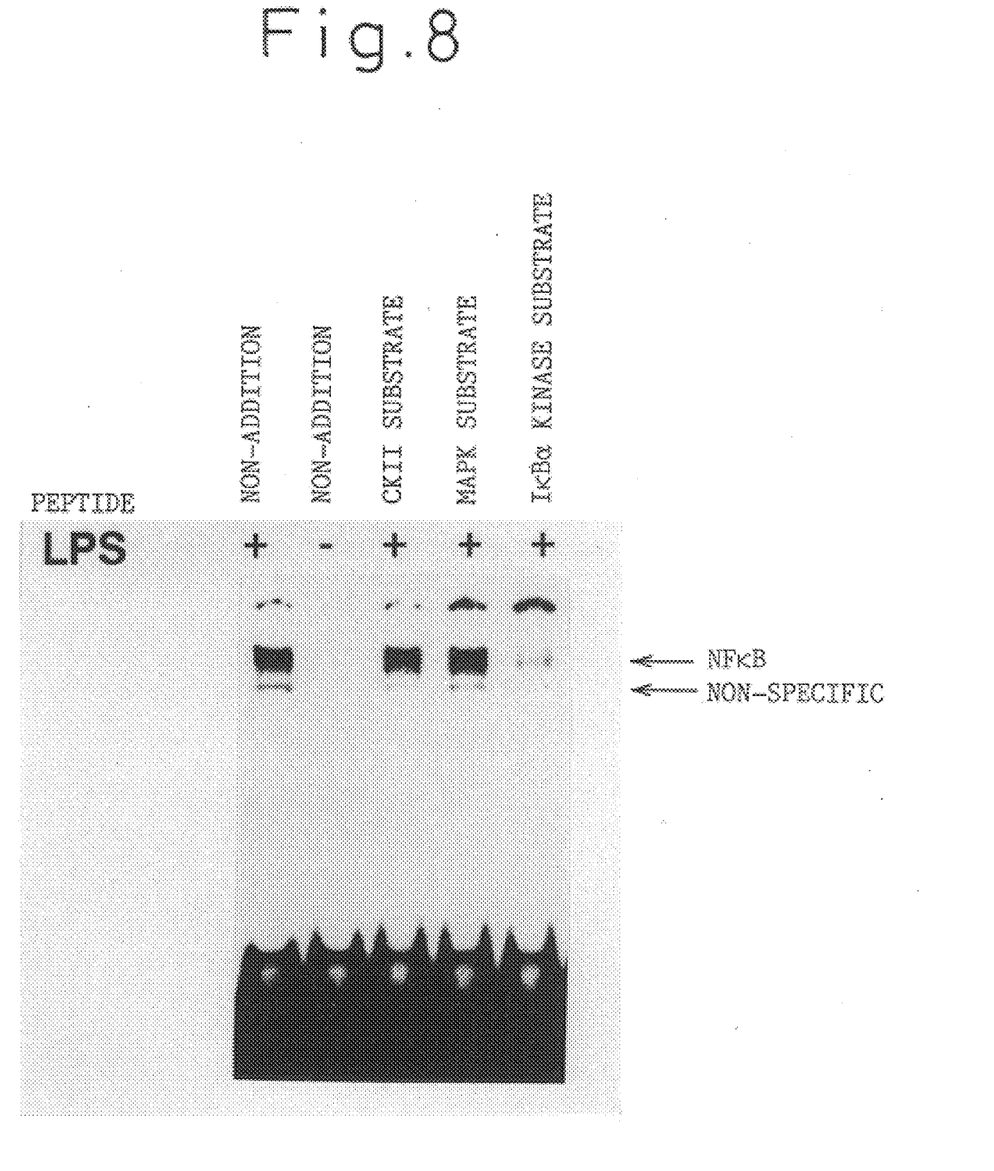
FIG. 8 illustrates a gel shift assay wherein the peptide corresponding with site of IκBα (IκBα kinase substrate) and control peptides which are a casein kinase substrate (CKII substrate) and MAP kinase substrate (MAPK substrate) were added.
Figure 9:
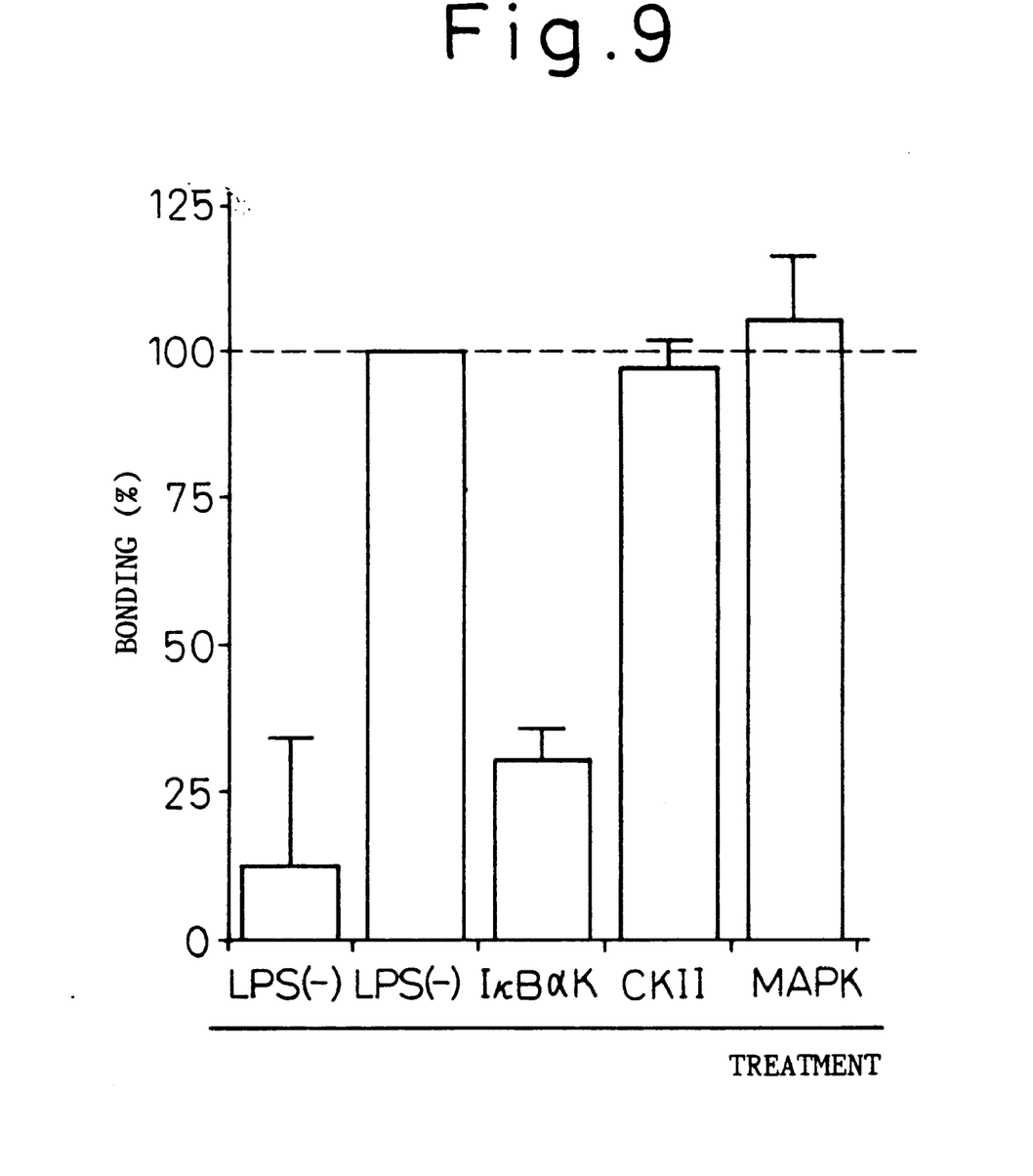
FIG. 9 illustrates the analysis and quantitative determination of a gel shift assay using an image analyzer in the case wherein the peptide of the phosphorylation site of IκBα (IκBαK) and control peptides consisting of casein kinase substrate (CKII substrate) and MAP kinase substrate (MAPK substrate) were added. The relative ratio of each treatment group is shown when that of the LPS(+)/peptide non-addition group is taken to be 100% (n=4).

The results of gel shift assay are shown in FIG. 8. In the system in which THP-1 cells stimulated with LPS were used, phosphorylation of IκBα was inhibited in the group to which was added IκBα phosphorylation site peptide, and as a result, NFκB activity was not observed. Moreover, analysis and quantification results with the image analyzer are shown in FIG. 9. NFκB activity was clearly inhibited in the group to which was added IκBα phosphorylation site peptide.

Industrial Applicability

According to the present invention, an antiinflammatory agent and immunosuppressant are provided that are effective in treatment of diseases involving inflammatory cytokines and inflammatory mediators including inflammatory diseases such as multiple sclerosis, systemic lupus erythematosus, and rejection reactions during bone marrow transplantation and organ transplantation.

The peptide or its salt contained as an active ingredient of the antiinflammatory agent and immunosuppressant provided by the present invention inhibits phosphorylation of IκBα, which as a result of inhibiting the effect of transcription activation by NFκB, is able to alleviate the above-mentioned diseases by administering to patients suffering from said diseases.

---

We claim:

1. A peptide which inhibits phosphorylation activity of human IκBα and consists of the amino acid sequence of SEQ ID NO: 1, or a pharmaceutically acceptable salt thereof.

2. A peptide which inhibits phosphorylation activity of human IκBα and consists of the amino acid sequence of SEQ ID NO: 2, or a pharmaceutically acceptable salt thereof.

3. A peptide which inhibits phosphorylation activity of human IκBα and consists of the amino acid sequence of SEQ ID NO: 3, or a pharmaceutically acceptable salt thereof.

4. A peptide which inhibits phosphorylation activity of human IκBα and consists of the amino acid sequence of SEQ ID NO: 4, or a pharmaceutically acceptable salt thereof.

5. A peptide which inhibits phosphorylation activity of human IκBα, which is a fragment of the amino acid sequence of SEQ ID NO: 1 and which comprises the amino acid sequence of SEQ ID NO: 4, or a pharmaceutically acceptable salt thereof.

6. A peptide which inhibits phosphorylation activity of human IκBα, which is a fragment of an amino acid sequence modified from the amino acid sequence of SEQ ID NO: 1, and which comprises an amino acid sequence of SEQ ID NO: 4, wherein said modification from the amino acid sequence of SEQ ID NO: 1 is a replacement and/or deletion of one or more amino acids in SEQ ID NO: 1 other than the amino acids in SEQ ID NO: 4, or a pharmaceutically acceptable salt thereof.

7. A composition for inhibition of phosphorylation activity of human IκBα, comprising a peptide according to claim 1.

8. A composition for inhibition of phosphorylation activity of human IκBα, comprising a peptide according to claim 2.

9. A composition for inhibition of phosphorylation activity of human IκBα, comprising a peptide according to claim 3.

10. A composition for inhibition of phosphorylation activity of human IκBα, comprising a peptide according to claim 4.

11. A composition for inhibition of phosphorylation activity of human IκBα, comprising a peptide according to claim 5.

12. A composition for inhibition of phosphorylation activity of human IκBα, comprising a peptide according to claim 6.

13. An immunosuppressant composition comprising a peptide according to claim 1.

14. An immunosuppressant composition comprising a peptide according to claim 2.

15. An immunosuppressant composition comprising a peptide according to claim 3.

16. An immunosuppressant composition comprising a peptide according to claim 4.

17. An immunosuppressant composition comprising a peptide according to claim 5.

18. An immunosuppressant composition comprising a peptide according to claim 6.

19. An immunosuppressant composition comprising a peptide or a salt thereof according to claim 1.

20. An immunosuppressant composition comprising a peptide or a salt thereof according to claim 2.

21. An immunosuppressant composition comprising a peptide or a salt thereof according to claim 3.

22. An immunosuppressant composition comprising a peptide or a salt thereof according to claim 3.

23. An immunosuppressant composition comprising a peptide or a salt thereof according to claim 4.

24. An immunosuppressant composition comprising a peptide or a salt thereof according to claim 5.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS:
      (D) TOPOLOGY: linear    (ii) MOLECULE TYPE: peptide    (xi) SEQUENCE DESCRIPTION: SEQ ID NO:1:

Met Leu Pro Glu Ser Glu Asp Glu Glu Ser Tyr Asp Thr Glu Ser Glu
   1            5                     10                  15

Phe Thr Glu Phe Thr Glu Asp Glu Leu
             20                  25

(2) INFORMATION FOR SEQ ID NO:2:

(i) SEQUENCE CHARACTERISTICS:
      (A) LENGTH: 17 amino acids
      (B) TYPE: amino acid
      (C) STRANDEDNESS:
      (D) TOPOLOGY: linear    (ii) MOLECULE TYPE: peptide    (xi) SEQUENCE DESCRIPTION: SEQ ID NO:2:

```
    Met Leu Pro Glu Ser Glu Asp Glu Glu Ser Tyr Asp Thr Glu Ser Glu
    1               5                   10                  15

Phe (2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Ser Glu Asp Glu Glu Ser Tyr Asp Thr Glu Ser Glu Phe
    1               5                   10

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Ser Tyr Asp Thr Glu Ser
    1               5

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:5:

GCGAATTCCA TGTTCCAGGC GGCCGAGCG                                          29

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:6:

GCAGGATCCT CATAACGTCA GACGCTGGC                                          29

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear
```

-continued (ii) MOLECULE TYPE: other nucleic acid
            (A) DESCRIPTION: /desc = "Synthetic DNA"

(xi) SEQUENCE DESCRIPTION: SEQ ID NO:7:

GCAGGATCCT CAATCAGCCC CACACTTCAA CAG                33

(2) INFORMATION FOR SEQ ID NO:8:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:8:

GCAGGATCCT CAGTAGTTGG TAGCCTTCAG GAT                33

(2) INFORMATION FOR SEQ ID NO:9:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:9:

GCGAATTCCG ACGGGGACTC GTTCCTGCA                     29

(2) INFORMATION FOR SEQ ID NO:10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:10:

GCGAATTCCA ATGGCCACAC GTGTCTACAC                    30

(2) INFORMATION FOR SEQ ID NO:11:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:11:

GCAGGATCCT CAGAACTCTG ACTCTGTGTC ATA                33

(2) INFORMATION FOR SEQ ID NO:12:

(i) SEQUENCE CHARACTERISTICS:
            (A) LENGTH: 33 base pairs
            (B) TYPE: nucleic acid (C) STRANDEDNESS: single
        (D) TOPOLOGY: linear (ii) MOLECULE TYPE: other nucleic acid
        (A) DESCRIPTION: /desc = "Sythetic DNA"

(xi) SEQUENCE DESCRIPTION: SEQ ID NO:12:

GCAGGATCCT CACTCTGGCA GCATCTGAAG GTT                          33

(2) INFORMATION FOR SEQ ID NO:13:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Met Leu Pro Glu Ala Glu Asp Glu Glu Ser Tyr Asp Thr Glu Ser Glu
    1               5                   10                  15

Phe Thr Glu Phe Thr Glu Asp Glu Leu
                20                  25

(2) INFORMATION FOR SEQ ID NO:14:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Met Leu Pro Glu Ser Glu Asp Glu Glu Ala Tyr Asp Thr Glu Ser Glu
    1               5                   10                  15

Phe Thr Glu Phe Thr Glu Asp Glu Leu
                20                  25

(2) INFORMATION FOR SEQ ID NO:15:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Met Leu Pro Glu Ser Glu Asp Glu Glu Ser Tyr Asp Ala Glu Ser Glu
    1               5                   10                  15

Phe Thr Glu Phe Thr Glu Asp Glu Leu
                20                  25

(2) INFORMATION FOR SEQ ID NO:16:

(i) SEQUENCE CHARACTERISTICS:
        (A) LENGTH: 25 amino acids
        (B) TYPE: amino acid
        (C) STRANDEDNESS:
        (D) TOPOLOGY: linear -continued (ii) MOLECULE TYPE: peptide (xi) SEQUENCE DESCRIPTION: SEQ ID NO:16:

Met Leu Pro Glu Ser Glu Asp Glu Glu Ser Tyr Asp Thr Glu Ala Glu
    1               5                   10                  15

Phe Thr Glu Phe Thr Glu Asp Glu Leu
                20                  25

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Arg Arg Arg Glu Glu Glu Thr Glu Glu Glu
    1               5                   10

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Ala Pro Arg Thr Pro Gly Gly Arg Arg
    1               5

(2) INFORMATION FOR SEQ ID NO:19:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

Met Leu Pro Glu Ser Glu Asp Glu Glu Ser Tyr Asp Thr Glu Ser Glu
    1               5                   10                  15

Phe Thr Glu Phe Thr Phe Asp Glu Leu Pro Tyr Asp Asp
                20                  25

(2) INFORMATION FOR SEQ ID NO:20:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Met Leu Pro Glu Ala Glu Asp Glu Glu Ala Tyr Asp Ala Glu Ala Glu
    1               5                   10                  15

Phe Ala Phe Phe Ala Glu Asp Glu Leu
                20                  25